US012254652B2

(12) United States Patent
Voigt et al.

(10) Patent No.: US 12,254,652 B2
(45) Date of Patent: Mar. 18, 2025

(54) METHOD FOR DETERMINING THE THREE-DIMENSIONAL POSITIONS OF POINTS IN A TARGET REGION ON A PATIENT IN A REFERENCE COORDINATE SYSTEM OF A SURGICAL VISUALIZATION SYSTEM AND SURGICAL VISUALIZATION SYSTEM

(71) Applicant: Carl Zeiss Meditec AG, Jena (DE)

(72) Inventors: Christian Voigt, Abtsgmünd (DE); Dominik Litsch, Schorndorf (DE)

(73) Assignee: Carl Zeiss Meditec AG, Jena (DE)

( * ) Notice: Subject to any disclaimer, the term of this patent is extended or adjusted under 35 U.S.C. 154(b) by 76 days.

(21) Appl. No.: 18/121,185

(22) Filed: Mar. 14, 2023

(65) Prior Publication Data
US 2023/0298206 A1 Sep. 21, 2023

(30) Foreign Application Priority Data
Mar. 15, 2022 (DE) ...................... 10 2022 202 555.5

(51) Int. Cl.
*G06T 7/73* (2017.01)
*A61B 90/00* (2016.01)
(Continued)

(52) U.S. Cl.
CPC .............. *G06T 7/74* (2017.01); *A61B 90/361* (2016.02); *A61B 90/39* (2016.02);
(Continued)

(58) Field of Classification Search
CPC ......... G06T 7/74; A61B 90/361; A61B 90/39; G02B 21/0012; G02B 21/365
(Continued)

(56) References Cited

U.S. PATENT DOCUMENTS

| | | |
|---|---|---|
| 6,873,867 B2 | 3/2005 | Vilsmeier |
| 7,577,474 B2 | 8/2009 | Vilsmeier |
| (Continued) | | |

FOREIGN PATENT DOCUMENTS

| | | |
|---|---|---|
| DE | 102008052976 | 4/2010 |
| DE | 102018119343 | 2/2020 |
| (Continued) | | |

OTHER PUBLICATIONS

Catalogue of Brainlab concerning laser pointer Z-touch®, pp. 1-11.

*Primary Examiner* — Matthew David Kim
(74) *Attorney, Agent, or Firm* — NIXON PEABODY LLP; Jeffrey L. Costellia

(57) ABSTRACT

Disclosed is a method for determining the three-dimensional positions of points in a target region on a patient in a reference coordinate system of a surgical visualization system. The method includes generating at least one light marking in the target region. Using at least one imaging unit to capture at least one image representation containing the at least one light marking. Determining a three-dimensional position of the at least one light marking in the reference coordinate system proceeding from image coordinates of the light marking in the captured image representation, with the known pose of the at least one light source and/or the light path and the known pose of the at least one imaging unit being taken into account. Repeating measures multiple times, with a position of the at least one light marking within the target region being changed each time, and providing the determined three-dimensional positions.

16 Claims, 2 Drawing Sheets

(51) Int. Cl.
*G02B 21/00* (2006.01)
*G02B 21/36* (2006.01)
*H04N 23/56* (2023.01)

(52) U.S. Cl.
CPC ....... *G02B 21/0012* (2013.01); *G02B 21/365* (2013.01); *A61B 2090/3937* (2016.02); *G06T 2207/10012* (2013.01); *G06T 2207/10056* (2013.01); *G06T 2207/30004* (2013.01); *G06T 2207/30204* (2013.01); *H04N 23/56* (2023.01)

(58) Field of Classification Search
USPC .......................................................... 348/47
See application file for complete search history.

(56) References Cited

U.S. PATENT DOCUMENTS

| | | | |
|---|---|---|---|
| 7,912,532 | B2 | 3/2011 | Schmidt et al. |
| 10,846,883 | B2 | 11/2020 | Urban et al. |
| 11,701,095 | B2* | 7/2023 | Lennartz ............... A61F 5/0083 606/170 |
| 2002/0002330 | A1* | 1/2002 | Vilsmeier ............. A61B 34/20 600/407 |
| 2005/0143645 | A1 | 6/2005 | Vilsmeier |
| 2006/0122516 | A1* | 6/2006 | Schmidt ................. A61B 90/39 600/476 |
| 2008/0097155 | A1* | 4/2008 | Gattani ................. A61B 5/065 600/117 |
| 2015/0332465 | A1* | 11/2015 | Schmidt ................ G01S 5/0247 348/169 |
| 2017/0156800 | A1* | 6/2017 | Brown ................. A61B 6/4441 |
| 2018/0014851 | A1* | 1/2018 | Hansen ............... A61B 17/3421 |
| 2018/0263710 | A1* | 9/2018 | Sakaguchi ............. A61B 90/14 |
| 2019/0029765 | A1* | 1/2019 | Crawford ............. A61B 90/361 |
| 2019/0201159 | A1* | 7/2019 | Shelton, IV ............ H04L 69/28 |
| 2020/0051280 | A1* | 2/2020 | Urban ........................ G06T 7/50 |
| 2021/0038340 | A1* | 2/2021 | Itkowitz .............. A61B 34/25 |
| 2021/0161614 | A1* | 6/2021 | Elimelech ............. A61B 90/39 |
| 2021/0298566 | A1* | 9/2021 | Levy .................. A61B 1/00105 |
| 2022/0001544 | A1* | 1/2022 | Zhang .................. A61B 5/4082 |
| 2022/0079687 | A1* | 3/2022 | Sexson .................. A61B 34/20 |
| 2022/0172445 | A1* | 6/2022 | Chen ...................... A61B 90/36 |
| 2022/0354597 | A1* | 11/2022 | Kaouk .................... G06T 7/248 |

FOREIGN PATENT DOCUMENTS

| | | |
|---|---|---|
| EP | 1142536 | 10/2001 |
| WO | WO-03/105709 | 12/2003 |
| WO | WO-2013/152790 | 10/2013 |

\* cited by examiner

METHOD FOR DETERMINING THE THREE-DIMENSIONAL POSITIONS OF POINTS IN A TARGET REGION ON A PATIENT IN A REFERENCE COORDINATE SYSTEM OF A SURGICAL VISUALIZATION SYSTEM AND SURGICAL VISUALIZATION SYSTEM

CROSS-REFERENCE TO RELATED APPLICATIONS

The present application claims priority under 35 U.S.C. § 119 to German Patent Application No. 10 2022 202 555.5, filed Mar. 15, 2022, the contents of which are incorporated by reference herein in their entirety.

The invention relates to a method for determining the three-dimensional positions of points in a target region on a patient in a reference coordinate system of a surgical visualization system and to a surgical visualization system.

A registration of a patient in a reference coordinate system is required for intraoperative navigation.

EP 1 142 536 A1 has disclosed a method for referencing a patient or a body part of a patient in a camera-assisted, medical navigation system, including the following steps: the body part of the patient to be referenced is brought into the capture region of a navigation system assisted by at least two cameras, with the navigation system capturing the three-dimensional spatial positions of light markings with computer assistance, a light beam is used to generate light markings on the surface of the body part to be referenced, with the three-dimensional position of said light markings being determined by the camera-assisted navigation system, the spatial pose of the surface of the body part to be referenced is determined using the position data for the light markings. Further, the invention relates to an apparatus for carrying out the method.

DE 10 2008 052 976 A1 has disclosed a tracking system for determining the position and/or orientation of an object, wherein the tracking system comprises means for generating a light point grid, means for projecting the light point grid onto the object, means for recording images and an evaluation unit for determining the position of the light points in the recorded images and for calculating the position and/or orientation of the object on the basis of the position of the light points.

However, the known methods and systems need to be additionally procured, and this is linked with additional outlay, additional costs and an additional used or occupied footprint at the site of operation.

The invention is based on the object of specifying a method and an apparatus which can be used to determine three-dimensional positions of points in a target region on a patient in a reference coordinate system, with however the method and the apparatus in particular requiring less outlay and being more cost-effective, and reducing a required footprint.

According to the invention, the object is achieved by a method having the features of Patent claim 1 and a surgical visualization system having the features of Patent claim 15. Advantageous configurations of the invention are evident from the dependent claims.

One of the basic concepts of the invention lies in the use of at least one light source of a surgical visualization system to generate at least one light marking in a target region on a patient. This at least one light marking is captured by means of at least one imaging unit of the surgical visualization system. To this end, the at least one imaging unit captures an image representation of the target region, said image representation containing the at least one light marking. A pose of the at least one light source and/or a light path between the at least one light source and the at least one light marking and a pose of the at least one imaging unit are known in a reference coordinate system of the surgical visualization system in each case, at least during the generation of the at least one light marking and the capture of the light marking. A three-dimensional position of the at least one light marking in the reference coordinate system is determined proceeding from image coordinates at which the at least one light marking appears in the captured at least one image representation and proceeding from the known poses and/or the known light path. This is implemented, in particular, taking account of the geometric arrangement of light source and/or light path and the at least one imaging unit, which geometric arrangement is known from the poses and allows the three-dimensional position within the reference coordinate system to be deduced from the image coordinates in the captured at least one image representation. Since the at least one light marking appears on a surface (e.g., face, back of the head, etc.), the three-dimensional position of the at least one light marking coincides with a position on the surface. Three-dimensional positions of points on the surface in the target region can therefore be determined from the positions of the light markings. The generation of the at least one light marking, the capture of an image representation containing the latter and the above-described evaluation of the captured image representation for the purpose of determining the three-dimensional position of the at least one light marking are therefore repeated, with a position of the at least one light marking being changed during each iteration. In this case, a profile of the surface in the target region can be scanned incrementally by means of the at least one light marking in order to determine the three-dimensional positions of the points on the surface in the target region. The three-dimensional positions determined for the points of the target region in the reference coordinate system are provided on the basis of the light markings.

Subsequently, provision can be made for the set of determined three-dimensional positions to be used to reconstruct a surface contour and/or to register three-dimensional measurement data of the patient captured by means of computed tomography (CT) and/or by means of any other imaging method (e.g., MRI etc.) with the set of three-dimensional positions such that these measurement data can be overlaid on the image representations captured by means of the surgical visualization system, for example for augmentation purposes.

In particular, a method for determining the three-dimensional positions of points in a target region on a patient in a reference coordinate system of a surgical visualization system is made available, comprising:

a) generating at least one light marking by means of at least one light source of the surgical visualization system in the target region, with a pose of the at least one light source in the reference coordinate system and/or a light path in the reference coordinate system being known, b) using at least one imaging unit of the surgical visualization system to capture at least one image representation containing the at least one light marking generated in the target region, with a pose of the at least one imaging unit in the reference coordinate system being known, c) determining a three-dimensional position of the at least one light marking in the reference coordinate system proceeding from image coordinates of the at least one light marking in the captured at least one image representation, with the known pose of the at least one light source and/or the respectively associated light path and the known pose of the at least one imaging unit being taken into account, d) repeating measures a) to c) multiple times, with a position of the at least one light marking within the target region being changed each time, providing the three-dimensional positions determined for the points of the target region in the reference coordinate system on the basis of the light markings.

Further, a surgical visualization system, in particular, is developed, comprising a medical microscope, having at least one light source which is configured to generate at least one light marking in a target region on a patient, with a pose of the at least one light source in a reference coordinate system of the surgical visualization system and/or a light path in the reference coordinate system being known; and at least one imaging unit which is configured to capture at least one image representation containing the at least one light marking generated in the target region, with a pose of the at least one imaging unit in the reference coordinate system being known; and a data processing device, with the data processing device being configured to determine three-dimensional positions of points in the target region in the reference coordinate system of the surgical visualization system, to determine a three-dimensional position of the generated at least one light marking in the reference coordinate system proceeding from image coordinates of the at least one light marking in the captured at least one image representation, with the known pose of the at least one light source and/or the respectively associated light path and the known pose of the at least one imaging unit being taken into account, to prompt multiple repetition of the generation and capture of the at least one light marking in the target region and determination of the three-dimensional position, and, in this respect, to prompt a respective change in a position of the at least one light marking within the target region during each repetition, and to provide the three-dimensional positions determined for the points of the target region in the reference coordinate system on the basis of the light markings.

An advantage of the method and the surgical visualization system is that there is no need to procure additional devices, for example a navigation system or a tracking system, in order to determine three-dimensional positions of points within a target region on a patient. As a result, it is possible to save both costs and a required footprint. The three-dimensional positions of the points in the target region are advantageously determined by means of the surgical visualization system itself.

A further advantage of the use of the at least one imaging unit of the surgical visualization system lies in the fact that it is possible to improve an accuracy when determining the three-dimensional positions. External camera-assisted navigation systems are situated at a greater distance from the target region on the patient as these often have to capture a relatively large region around the patient. By contrast, the at least one imaging unit (i.e., an associated imaging optical unit in particular) is arranged in the direct vicinity at a small work distance from the target region since highly resolving image representations of the target regions generally have to be captured in order to assist a surgeon during an operation by means of the surgical visualization system. Further, external camera-assisted navigation systems generally have a relatively large capture region, whereas the at least one imaging unit only captures the target region on the patient.

As a result of the shorter work distance from the target region and the smaller capture region, it is possible in particular to reduce the size of the light marking, which improves the accuracy, in particular a spatial resolution. Furthermore, the capture is implemented directly in the reference coordinate system in particular and without reference to a world coordinate system.

Further, a surgeon can be unburdened as a result of automation in relation to the determination of the three-dimensional positions of the points in the target region, which is realized by the method and the surgical visualization system.

A pose denotes, in particular, a six-dimensional coordinate which comprises a three-dimensional position in the reference coordinate system of the surgical visualization system and a three-dimensional alignment (e.g., in the form of a roll, pitch and yaw angle) in the reference coordinate system. The known pose of the at least one imaging unit in particular allows the localization of possible three-dimensional original features, which are contained in an image representation, in space on the basis of associated image coordinates of the image representation. Expressed differently, each image coordinate (or each pixel) in a captured image representation can be assigned a solid angle, from which an image value of the image coordinate or pixel can obtain its information. In this case, an extrinsic and an intrinsic calibration of the at least one imaging unit, in particular, are taken into account. A known pose of the at least one light source and/or a known light path of the light emitted by the at least one light source allow the determination of three-dimensional positions in the reference coordinate system for possible points of incidence, at which the at least one light marking is incident on a surface and is specularly or diffusely reflected from there. Expressed differently, a respective solid angle is known, in which a light generated by the at least one light source for generating the at least one light marking is emitted. Using the possible original positions and the possible points of incidence, it is then possible, using methods known per se, to determine the three-dimensional position of the at least one light marking in the reference coordinate system on the basis of the point of intersection, that is to say the point where the aforementioned solid angles cross. Expressed differently, the three-dimensional position is determined in particular by way of triangulation. In principle, however, the three-dimensional position of the at least one light marking may also be determined differently. The additional imaging units are taken into consideration accordingly in the case of more than one imaging unit.

The pose of the at least one light source, the respectively assigned light path and the pose of the at least one imaging unit are determinable, for example, by way of a calibration in the reference coordinate system provided to this end. Further, the sensor systems configured to this end may also be provided for determining the poses and/or the light path. By way of example, such sensor systems may be arranged on the at least one light source and/or on the at least one imaging unit and/or on a respective imaging optical unit, and can detect the respective actual state thereof and provide the latter in the form of appropriate data.

In particular, the at least one light marking comprises an individual light spot. However, in principle, the at least one light marking may also comprise more complex light patterns, for example a point grid, etc. The at least one light marking may have a wavelength or a wavelength range which is able to be located both in the visible and in the invisible spectral range, provided the at least one imaging unit is able to capture this wavelength (range).

Parts of the surgical visualization system, in particular the data processing device, can be embodied, either individually or together, as a combination of hardware and software, for example as program code that is executed on a microcontroller or microprocessor. However, provision can also be made for parts to be designed as application-specific integrated circuits (ASICs) and/or field-programmable gate arrays (FPGAs), either on their own or in combination.

In an embodiment, provision is made for the poses of the at least one light source and the at least one imaging unit to be fixed relative to one another at least while carrying out measures a) to d), with the at least one light source being moved together with the at least one imaging unit within the scope of measure d) for the purpose of changing the position of the at least one light marking. In this way, the position of the at least one light marking can be changed without a pose of the at least one light source having to be changed to this end. In particular, the at least one light source and the at least one imaging unit are jointly displaced to this end, with the result that the target region is scanned incrementally by means of the at least one light marking. The change in the position of the at least one light marking can be implemented in the simplest case by way of a manual change in the positions of the at least one light source and the at least one imaging unit. A further advantage of this embodiment can be found in the fact that the at least one imaging unit needs to capture a smaller part of the target region in order to reliably capture the light marking as a result of the fixation and the joint movement, whereby a resolution during the capture can be increased. Further, there are fewer parts that are movable in relation to one another and hence fewer accompanying faults (e.g., play, wear), whereby a more robust calibration can be achieved. Moreover, an actuator system requires fewer component parts since the at least one light source and the at least one imaging unit are jointly moved. When using a robotic actuator system (robotic stand), it is further possible to influence the light path independently of the position of the at least one light marking on the patient, whereby the determination of the three-dimensional positions around the patient (e.g., behind the ear, from the side, etc.) is improved. In particular, what can be achieved hereby is that the at least one light marking is generated by light incident perpendicularly on a skin or surface of the patient, whereby a resolution can be improved since the at least one light marking then has the smallest extent. Further, it is easily possible to capture a plurality of image representations of one light marking, with the result that the determination of the three-dimensional position can be further improved. In particular, provision can be made for the poses of the at least one light source and the at least one imaging unit to be fixed relative to one another even during normal operation.

In a refined embodiment, provision is made for the change in the position to be implemented manually. By way of example, a surgeon or an assistant can change the position of the at least one light marking by changing the poses (fixed relative to one another) of the at least one light source and the at least one imaging unit.

In another refined embodiment, provision is made for the change in the position to be implemented in automated fashion by means of a robotic actuator system of the surgical visualization system. As a result, the target region can be scanned in automated fashion. In this case, a specified increment for the positions of the at least one light marking in the target region, for example, can be chosen. In particular, the robotic actuator system can incrementally scan the at least one target region to this end. By using the robotic actuator system, it is possible in particular to improve a resolution when determining the three-dimensional position of the points in the target region since positions can be set in more targeted fashion. In particular, the robotic actuator system is not moved during the capture. By way of example, the robotic actuator system is controlled by the data processing device and/or a controller of the surgical visualization system. By controlling the robotic actuator system, there is a change in a pose of the at least one light source and an associated light path and a pose of the at least one imaging unit. By way of example, the robotic actuator system may be equipped with a sensor system, with the (changed) poses and/or the (changed) light path being able to be determined from the sensor data thereof.

In an embodiment, provision is made for the change in the position of the at least one light marking in measure d) to comprise a change in a pose of the at least one light source and/or a change in the light path of a light emanating from the at least one light source. As a result, the at least one light marking can be generated at different positions within the target region without this requiring a change in a pose of other parts of the surgical visualization system. In this case, the pose of the at least one light source and/or the respective associated light path and the pose of the at least one imaging unit need not be fixed in relation to one another. By way of example, a pose of the at least one light source can be changed under open-loop or closed-loop control by means of an actuator system of the surgical visualization system configured to this end. By way of example, a light path can be changed under open-loop and/or closed-loop control by means of an imaging or a deflection optical unit (e.g., a mirror) correspondingly configured to this end. In particular, the open-loop and/or closed-loop control is implemented by means of the data processing device and/or by means of a controller of the surgical visualization system configured to this end.

In an embodiment, provision is made for the position to be successively changed in accordance with a set of predetermined positions. This makes it possible to ensure that a sufficiently large area of the target region is captured or scanned. Further, provision can also be made for there to be a marked area within the target region which is intended to be captured (or scanned) at a higher resolution such that a larger number of positions are provided per unit area there than in other areas for the at least one light marking. In this case, provision can also be made for an initial capture to be implemented with a lower, uniform resolution and, proceeding herefrom, the marked area is subsequently defined and captured with an increased resolution in order to increase the accuracy in this marked region.

In an embodiment, provision is made for the position upon repetition to be changed in such a way that at least one partial region of the target region is scanned. What this can achieve is that at least the partial region of the target region is captured completely, that is to say without gaps in relation to a specified resolution or increment between individual positions of the at least one light marking. In particular, provision is made for the entire target region to be scanned. Scanning can be implemented both by changing the pose of the at least one light source and/or the associated light path and by jointly changing the poses, fixed relative to one another, of the at least one light source and the at least one imaging unit, for example by way of an incremental control of a robotic actuator system.

In an embodiment, provision is made for at least one quality value to be determined proceeding from the captured image representations and/or the three-dimensional points determined for the points in the target region, with the three-dimensional positions of the target region being at least partially determined anew if the determined at least one quality value drops below an associated specified minimum quality value. As a result, the quality of the determined three-dimensional positions can be checked in a targeted fashion. In particular, the quality, expressed in the form of the determined at least one quality value, can be optimized in a targeted fashion. To determine the at least one quality value, provision can for example be made for the at least one imaging unit to evaluate captured image representations and determine an imaging sharpness as a quality value. Should the imaging sharpness not achieve a minimum sharpness specified as a minimum quality value, the at least one imaging unit may for example change parameters in order to increase the imaging sharpness. Subsequently, at least one image representation containing the at least one light marking is captured anew. Further, provision can be made for a pose of the at least one light source and/or a pose of the at least one imaging unit to be changed prior to a renewed determination. As a result, the target region may be captured from a different perspective, for example. This is based on the idea that a surface can be captured with a greater accuracy or higher resolution in the case of a perpendicular capture (i.e., in the direction of a surface normal of the surface) than in the case of a non-perpendicular capture.

A quality value may also be determined starting from an error value or confidence value determined when determining the positions.

Further, the at least one quality value can be determined taking account of three-dimensional measurement data from an imaging method (CT, MRI, etc.). To this end, a registration for example is carried out between the three-dimensional positions of the points in the target region as determined by means of the method and three-dimensional data of the target region as determined by means of the imaging method, with a deviation of the points with respect to one another, for example in the form of a mean deviation (e.g., mean square error), being determined and used as a quality value.

Provision can also be made for the determination of the three-dimensional positions of the points in the target region for at least a portion of the target region to be followed by the addition of further positions, for which light markings are generated and captured in the target region, as additional sampling points for a subsequent registration with three-dimensional data of an imaging method in order to increase resolution in at least the partial region of the target region. Provision can also be made for the same positions to be captured from a different direction and/or in a different orientation. In particular, this may be the case if it turns out that one or more degrees of freedom were not captured with a sufficient quality. In particular, a degree of freedom in this case is a dimension of the pose of the patient, that is to say a translational position or a rotational orientation of the patient in the reference coordinate system.

In an embodiment, provision is made for at least one laser to be used as at least one light source. This enables the generation of a punctiform light marking in the target region, which is of the order of millimetres in terms of its dimensions. In particular, this can increase in accuracy when determining the positions of the points in the target region since the approximately punctiform light marking in particular has a smaller area than, for example, a planar marking in the case of which there is averaging over a relatively large, non-planar area of the generated light marking in order to determine the position of the light marking in a captured image representation.

In a refined embodiment, provision is made for the at least one laser to also serve to ascertain a focal distance. In particular, a laser regularly used for the adjustment of a focus or a work distance of an imaging optical unit can then also be used as a laser (or as a light source).

In an embodiment, provision is made for the change in the position of the at least one light marking in measure d) to comprise defocussing. In particular, provision can be made in this context for two lasers used for focussing purposes by being made to fully overlap in the captured region (i.e., in particular the target region in the present case) to this end to be used to generate the respective light markings at different positions in the target region by way of targeted defocussing. The defocussing causes the light markings of the two lasers, which otherwise are overlaid at the same position in the target region, to be able to be moved to different positions within the target position. In particular, the two light markings then move away from one another from an initially identical position in the case of targeted defocussing. If the two (or more) lasers can be controlled on an individual basis, they can also be moved on an individual basis to the respective positions within the target region in order to generate a light marking there in each case.

In an embodiment, provision is made for at least two imaging units to be used, with the at least two imaging units being cameras of the surgical visualization system.

In a refined embodiment, provision is made for the at least two cameras to be part of a stereo camera of the surgical visualization system.

In an embodiment, provision is made for at least one of the cameras to be a surround camera of the surgical visualization system. In this case, a surround camera refers to, in particular, a camera which is operated independently of an imaging optical unit of a main observer beam path of the medical microscope in order to additionally also capture an immediate surround of a target region and, as a result, for example also capture surgical instruments in addition to the target region. In particular, provision can be made for at least one camera of a stereo camera system of the surgical visualization system and the surround camera to be used to carry out the method.

In an embodiment, provision is made for at least one marking securely arranged on the patient to be captured by means of the at least one imaging unit in addition to the at least one light marking, with a pose of the at least one marking in the reference coordinate system being determined and provided. As a result, it is possible to additionally determine a relationship between the determined three-dimensional position of the points in the target region and the marking (which is also referred to as a patient target). As a result, the patient can be captured relative to the surgical visualization system, in particular the surgical microscope, even if said patient is largely covered by a sterile cover. Consequently, this facilitates the capture of the covered patient and further also facilitates a localization of the determined three-dimensional positions of the points in the target region if the patient is repositioned (together with the marking) and then captured from a different direction.

Further features relating to the configuration of the surgical visualization system arise from the description of configurations of the method. The advantages of the surgical visualization system here are in each case the same as for the configurations of the method.

The invention is explained in greater detail below on the basis of preferred exemplary embodiments with reference to the figures. In the figures:

FIG. 1 shows a schematic representation of an embodiment of the surgical visualization system 1. The surgical visualization system 1 is configured to carry out the method described in this disclosure.

Figure 1:
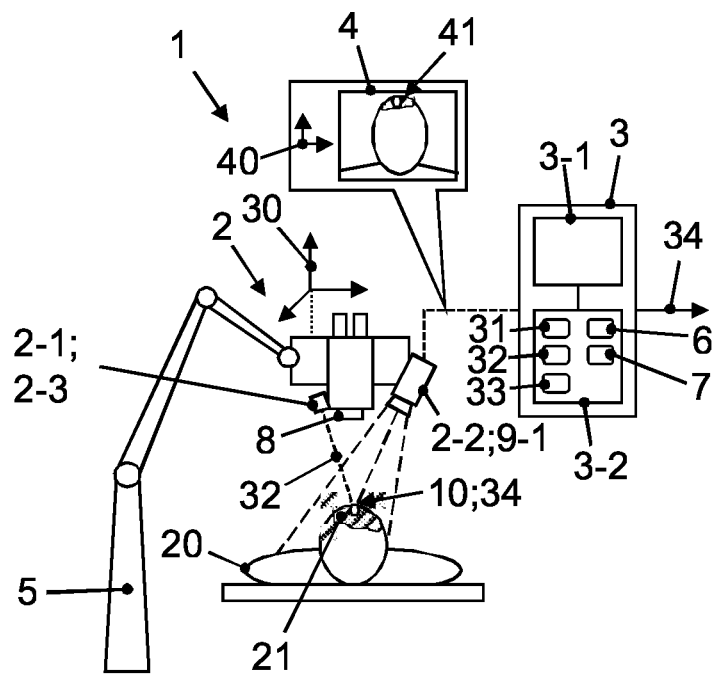
FIG. 1 shows a schematic representation of embodiments of the surgical visualization system.

The surgical visualization system 1 comprises a medical microscope 2, for example a surgical microscope, and a data processing device 3.

The medical microscope 2 comprises a light source 2-1 and an imaging unit 2-2. The light source 2-1 is configured to generate at least one light marking 10 in a target region 21 on a patient 20. A pose 31 of the light source 2-1 in a reference coordinate system 30 and/or a light path 32 in the reference coordinate system 30 is known. The imaging unit 2-2 is configured to capture at least one image representation 4 containing the at least one light marking 10 generated in the target region 21. A pose 33 of the imaging unit 2-2 in the reference coordinate system 30 is known.

The data processing device 3 comprises a computing device 3-1 and a memory 3-2. To determine three-dimensional positions 34 of points in the target region 21 in the reference coordinate system 30 of the surgical visualization system 1, the data processing device 3 is configured to determine a three-dimensional position 34 of the at least one generated light marking 10 in the reference coordinate system 30 proceeding from image coordinates 41 of the at least one light marking 10 in the captured at least one image representation 4, with the known pose 31 of the light source 2-1 and/or the respectively associated light path 32 and the known pose 33 of the imaging unit 2-2 being taken into account. The image coordinates 41 are coordinates in a two-dimensional image coordinate system 40 which for example contains a x-coordinate axis and a y-coordinate axis of pixels in the captured image representation 4.

Further, the data processing device 3 is configured to prompt multiple repetition of the generation and capture of the at least one light marking 10 in the target region 21 and determination of the three-dimensional position 34, and, in this respect, to prompt a respective change in a position of the at least one light marking 10 within the target region 21 during each repetition. In particular, the repetitions are implemented for a given number of positions.

The data processing device 3 provides the three-dimensional positions 34 determined for the points of the target region 21 in the reference coordinate system 30 on the basis of the light markings 10. By way of example, this is implemented as an analogue or digital signal, for example in the form of a data packet.

It is possible to estimate a surface contour of the target region 21 proceeding from the provided three-dimensional positions 34. Three-dimensional measurement data from an imaging method (e.g., CT, MRI, etc.) of the target region 21 can then be registered with the determined positions 34 or estimated surface contour on the basis thereof. During an operation, the three-dimensional measurement data can then be overlaid on the captured image representation 4 of the target region 21.

Provision can be made for the poses 31, 33 of the light source 2-1 and the imaging unit 2-2 to be fixed relative to one another, at least during the implementation of the generation of the at least one light marking 10 and the capture of the image representation 4, with the light source 2-1 being moved together with the imaging unit 2-2 for the purpose of changing the position of the at least one light marking 10 in order to repeat the measures. In particular, a respective light path 21 is also fixed relative to the at least one light source 2-1 and at least one imaging unit 2-2. To this end, the surgical visualization system 1 in particular comprises a robotic actuator system 5, which is designed in the embodiment shown as a multi-link and multi-joint robotic arm, on which the medical microscope 2 is arranged. The position of the at least one light marking 10 in the target region 21 is changed by controlling the robotic actuator system 5. The reference coordinate system 30 is also moved in the process. This changes a position of the at least one light marking 10 in the target region 21 because the light source 2-1 and imaging unit 2-2 move relative to the patient 20. As a result, different positions can be marked with a light marking 10 within the target region 21 such that a respectively associated three-dimensional position 34 on the patient 20 can be determined within the reference coordinate system 30.

Provision can be made for the position of the at least one light marking 10 to be changed successively in accordance with a set of predetermined positions. By way of example, in this case provision can be made for more positions, for example, to be homed in on for partial regions within the target region 21 than in the remaining partial regions, for example because a greater number of sampling points, that is to say a higher resolution, is desired there.

Provision can be made for the position of the at least one light marking 10 upon repetition to be changed in such a way that at least one partial region of the target region 21 is scanned. In particular, scanning in this case comprises line-by-line or column-by-column scanning of at least the partial region.

Provision can be made for at least one quality value 6 to be determined proceeding from the captured image representations 4 and/or the three-dimensional points 34 determined for the points in the target region 21, with the three-dimensional positions 34 of the target region 21 being at least partially determined anew if the determined at least one quality value 6 drops below an associated specified minimum quality value 7. The quality value 6 may comprise the quantities already described in the general description, with the minimum quality value 7 comprising a quantity corresponding therewith.

Provision can be made for a laser 2-3 to be used as a light source 2-1. In particular, this can be a laser diode.

Figure 2:
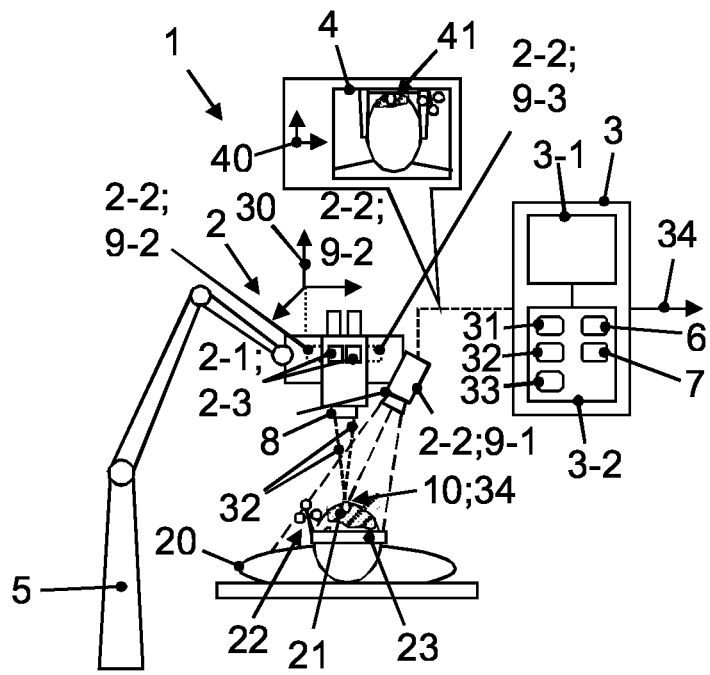
FIG. 2 shows a schematic representation of further embodiments of the surgical visualization system.

Provision can be made for the laser 2-3 also to serve to ascertain a focal distance of the medical microscope 2. In particular, provision can be made for two lasers 2-3 to be provided to this end, which lasers are imaged onto the target region 21 by an imaging optical unit 8. This is illustrated schematically in FIG. 2. The illustrated embodiment corresponds to the embodiment shown in FIG. 1. In this case, identical reference signs designate identical features and terms. The imaging optical unit 8 of the medical microscope 2 and/or the lasers 2-3 are then controlled in such a way that the light markings 10 generated by means of the two lasers 2-3 are made to fully overlap. What this can achieve is that the target region 21 is arranged at the correct focal distance from the imaging optical unit 8 of the medical microscope 2 and/or that a focal distance is known or able to be determined.

In particular, provision can be made for the one (or more) lasers 2-3 and/or the imaging optical unit 8 to be controllable in terms of a position and/or alignment. In this case, a position of the at least one light marking 10 can be changed by controlling the laser or lasers 2-3 and/or imaging optical unit 8.

Provision can be made for the change in the position of the at least one light marking 10 in measure d) to comprise defocussing. In particular, the two (or more) lasers 2-3 also used to determine a focal distance are used here to generate the at least one light marking 10. By way of example, provision can be made for a work distance of the medical microscope 2 from the target region 21 to be changed in order to attain a defocusing The light markings 10 of the two (or more) lasers 2-3 in the target region 21 made to fully overlap in the focus migrate apart during the defocussing, with the result that the positions of the light markings 10 change. Provision can alternatively or additionally be made for the positions of the light markings 10 to be changed by active control of the two (or more) lasers 2-3 if a position and/or an alignment of the two (or more) lasers 2-3 can be changed.

Provision can be made for at least two imaging units 2-2 to be used, with the at least two imaging units 2-3 being cameras 9-x of the surgical visualization system 1.

In particular, provision can be made for the at least two cameras 9-2, 9-3 to be part of a stereo camera of the surgical visualization system 1. In particular, provision can be made for the method to be carried out exclusively by means of the two cameras 9-2, 9-3 of the stereo camera.

However, provision can also be made for at least one of the cameras 9-x to be a surround camera 9-1 of the surgical visualization system 1. By way of example, provision can be made for the latter to be used in addition to the cameras 9-2, 9-3 of the stereo camera. This can improve quality when determining the positions 34 of the points in the target region 21.

Provision can be made for at least one marking 22 securely arranged on the patient 20 ("patient target") to be captured by means of the at least one imaging unit 2-2 in addition to the at least one light marking 10, with a pose of the at least one marking 22 in the reference coordinate system 30 being determined and provided. This is shown schematically in FIG. 2. There, the marking 22 is fastened to the head of the patient 20 by means of a clamp 23 such that said marking does not move relative to the head when the patient 20 or the head of the patient 20 is repositioned. This can allow a repositioning of the patient 20 without the positions 34 within the target region 21 having to be determined anew since already determined positions 34 can be converted (transformed) for the new pose of the target region 21 by way of the known pose of the marking 22 within the reference coordinate system 30.

Figure 3:
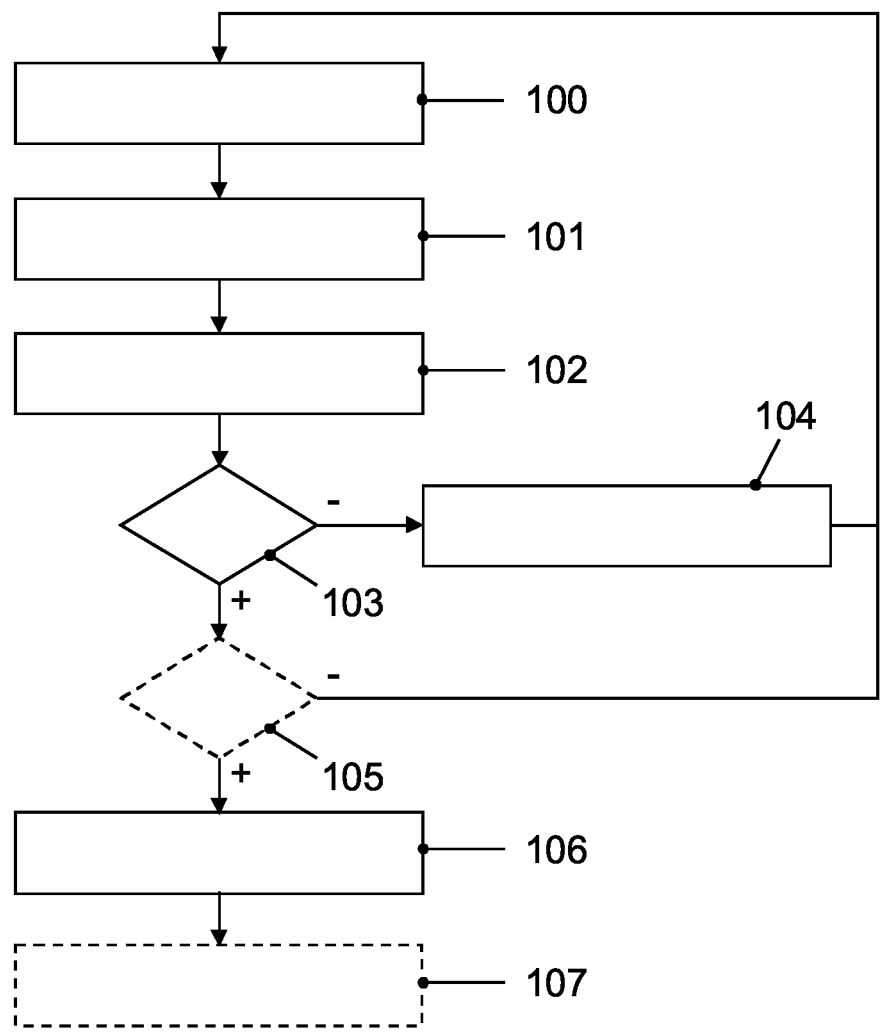
FIG. 3 shows a schematic flowchart of an embodiment of the method.

FIG. 3 shows a schematic flowchart of an embodiment of the method for determining the three-dimensional position of points in a target region on a patient in a reference coordinate system of a surgical visualization system. The method is carried out by means of one of the above-described embodiments of the surgical visualization system.

In a method step 100, at least one light marking is generated by means of at least one light source of the surgical visualization system in the target region, with a pose of the at least one light source in the reference coordinate system and/or a light path in the reference coordinate system being known.

In a method step 101, at least one imaging unit of the surgical visualization system is used to capture at least one image representation containing the at least one light marking generated in the target region, with a pose of the at least one imaging unit in the reference coordinate system being known.

In a method step 102, a three-dimensional position of the at least one light marking in the reference coordinate system is determined proceeding from image coordinates of the at least one light marking in the captured at least one image representation, with the known pose of the at least one light source and/or the respectively associated light path and the known pose of the at least one imaging unit being taken into account.

In a method step 103, a check is carried out as to whether a specified number of positions have already been determined for the target region. By way of example, provision can be made here for the target region to be at least partially scanned and/or raster scanned. In particular, a number of positions within the target region is defined in such a way here that a sufficient number of sampling points is available for the purpose of determining a surface contour of the target region on the patient (cf. method step 107).

If a given number of positions has not yet been captured, a position of the at least one light marking within the target region is changed in a method step 104, for example to the next position within a predetermined grid. Subsequently, method steps 100 to 103 are repeated.

By contrast, if the check in method step 103 yields that all positions have been determined, the three-dimensional positions determined for the points in the target region in the reference coordinate system on the basis of the light markings are provided in a method step 106. By way of example, this is implemented as an analogue or digital signal, for example in the form of a data packet.

In a method step 107, provision can be made for the provided points to be used to determine a surface of the target region within the reference coordinate system and carry out a registration of three-dimensional measurement data of an imaging method (CT, MRI, etc.) with the determined surface. Following the registration, it is possible to arrange the three-dimensional measurement data within the reference coordinate system and represent these overlaid on the target region. The three-dimensional measurement data can then be displayed to a surgeon in a manner overlaid with captured image representations of the target region in order to support a workflow in this way.

In a method step 105, provision can be made for at least one quality value to be determined proceeding from the captured image representations and/or the three-dimensional points determined for the points in the target region, with the three-dimensional positions of the target region being at least partially determined anew if the determined at least one quality value drops below an associated specified minimum quality value. The at least one quality value can also be determined on the basis of a registration, as described for method step 107, for example by virtue of a deviation of the individual registered points from one another being determined. If the check in method step 105 yields that the minimum quality value was undershot, the method is once again continued with method step 100, with the positions and/or changed positions of the target region being captured anew. By way of example, the light markings can be arranged on a different grid, with in particular a distance between the points of the grid being able to be changed. In this way, it is possible for example to increase the resolution during the capture and determination.

In method step 104, provision can be made for the at least one light source to be moved jointly with the at least one imaging unit for the purpose of changing the position of the at least one light marking. In this case, provision is made for the poses of the at least one light source and the at least one imaging unit to be fixed relative to one another, at least while carrying out measures 100, 101, 102 and 104. In particular, a light path is also fixed relative to the at least one light source and at least one imaging unit. The change in position is implemented, in particular, by means of a robotic actuator system of the surgical visualization system.

Alternatively, provision can be made in method step 104 for the change in the position of the at least one light marking in method step 104 to comprise a change in a pose of the at least one light source and/or a change in the light path of a light emanating from the at least one light source. By way of example, this can be implemented by means of actuator systems configured to this end, in particular under open-loop and/or closed-loop control by the data processing device and/or a controller of the surgical visualization system.

Further, provision can be made for method step 104 to additionally or alternatively provide for the change in the position of the at least one light marking to comprise (incrementally increasing) defocussing.

Provision can be made in method step 101 for at least one marking securely arranged on the patient to be captured by means of the at least one imaging unit in addition to the at least one light marking, with a pose of the at least one marking in the reference coordinate system being determined and provided.

LIST OF REFERENCE SIGNS

1 Surgical visualization system
2 Medical microscope
2-1 Light source
2-2 Imaging unit
2-3 Laser
3 Data processing device
3-1 Computing device
3-2 Memory
4 Image representation
5 Robotic actuator system
6 Quality value
7 Minimum quality value
8 Imaging optical unit
9-1 Surround camera
9-2 Camera (in particular of the stereo camera system)
9-3 Camera (in particular of the stereo camera system)
10 Light marking
20 Patient
21 Target region
22 Marking
23 Clamp
30 Reference coordinate system
31 Pose (light source)
32 Light path
33 Pose (imaging unit)
34 Three-dimensional position
40 Image coordinate system
41 Image coordinates
100-107 Method steps

The invention claimed is:
1. A method for determining three-dimensional positions of points in a target region on a patient in a reference coordinate system of a surgical visualization system, comprising:

a) generating at least one light marking by means of at least one light source of the surgical visualization system in the target region, with a pose of the at least one light source in the reference coordinate system and/or a light path in the reference coordinate system being known,
b) using at least one imaging unit of the surgical visualization system to capture at least one image representation containing the at least one light marking generated in the target region, with a pose of the at least one imaging unit in the reference coordinate system being known,
c) determining a three-dimensional position of the at least one light marking in the reference coordinate system proceeding from image coordinates of the at least one light marking in the captured at least one image representation, with the pose of the at least one light source and/or the respectively associated light path and the pose of the at least one imaging unit being taken into account,
d) repeating measures a) to c) multiple times, with a position of the at least one light marking within the target region being changed each time, and
providing the three-dimensional positions determined for the points of the target region in the reference coordinate system based on the light markings.

2. The method according to claim 1, wherein the pose of the at least one light source and the pose of at least one imaging unit are fixed relative to one another at least while carrying out measures a) to d), with the at least one light source being moved together with the at least one imaging unit within the scope of measure d) for the purpose of changing the position of the at least one light marking.

3. The method according to claim 1, wherein the change in the position is implemented in automated fashion by means of a robotic actuator system of the surgical visualization system.

4. The method according to claim 1, wherein the change in the position of the at least one light marking in measure d) comprises a change in the pose of the at least one light source and/or a change in the light path of a light emanating from the at least one light source.

5. The method according to claim 1, wherein the position is successively changed in accordance with a set of predetermined positions.

6. The method according to claim 1, wherein the position upon repetition is changed in such a way that at least one partial region of the target region is scanned.

7. The method according to claim 1, wherein at least one quality value is determined proceeding from the captured image representations and/or the three-dimensional points determined for the points in the target region, with the three-dimensional positions of the target region being at least partially determined anew if the determined at least one quality value drops below an associated specified minimum quality value.

8. The method according to claim 1, wherein at least one laser is used as at least one light source.

9. The method according to claim 8, wherein the at least one laser also serves to ascertain a focal distance.

10. The method according to claim 1, wherein the change in the position of the at least one light marking in measure d) comprises defocussing.

11. The method according to claim 1, wherein at least two imaging units are used, with the at least two imaging units being cameras of the surgical visualization system.

12. The method according to claim 11, wherein the at least two cameras are part of a stereo camera of the surgical visualization system.

13. The method according to claim 11, wherein at least one of the cameras is a surround camera of the surgical visualization system.

14. The method according to claim 1, wherein at least one marking securely arranged on the patient is captured by means of the at least one imaging unit in addition to the at least one light marking, with the pose of the at least one marking in the reference coordinate system being determined and provided.

15. The method according to claim 1, wherein the at least one light marking is a single light marking, the at least one light source is a single light source, and the at least one imaging unit of the surgical visualization system is a single imaging unit.

16. A surgical visualization system comprising:
a medical microscope having:
  at least one light source configured to generate at least one light marking in a target region on a patient, with a pose of the at least one light source in a reference coordinate system of the surgical visualization system and/or a light path in the reference coordinate system being known, and
  at least one imaging unit configured to capture at least one image representation containing the at least one light marking generated in the target region, with a pose of the at least one imaging unit in the reference coordinate system being known; and
a data processing device, with the data processing device being configured to:
  determine three-dimensional positions of points in the target region in the reference coordinate system of the surgical visualization system,
  determine a three-dimensional position of the generated at least one light marking in the reference coordinate system proceeding from image coordinates of the at least one light marking in the captured at least one image representation, with the pose of the at least one light source and/or the respectively associated light path and the pose of the at least one imaging unit being taken into account,
  prompt multiple repetition of the generation and capture of the at least one light marking in the target region and determination of the three-dimensional position,
  prompt a respective change in a position of the at least one light marking within the target region during each repetition, and
  provide the three-dimensional positions determined for the points of the target region in the reference coordinate system based on the light markings.

* * * * *